(12) United States Patent
Li et al.

(10) Patent No.: US 6,274,017 B1
(45) Date of Patent: Aug. 14, 2001

(54) BUFFER FOR ANALYZING SMALL INORGANIC CATIONS BY CAPILLARY ELECTROPHORESIS

(75) Inventors: Sam Fong Yau Li; Tianlin Wang, both of Singapore (SG)

(73) Assignee: National University of Singapore, Singapore (SG)

( * ) Notice: Subject to any disclaimer, the term of this patent is extended or adjusted under 35 U.S.C. 154(b) by 0 days.

(21) Appl. No.: 09/319,726

(22) PCT Filed: Dec. 9, 1997

(86) PCT No.: PCT/SG97/00067

§ 371 Date: Aug. 5, 1999

§ 102(e) Date: Aug. 5, 1999

(87) PCT Pub. No.: WO98/27422

PCT Pub. Date: Jun. 25, 1998

(30) Foreign Application Priority Data

Dec. 14, 1996 (SG) .................................................. 96117304

(51) Int. Cl.⁷ .................................................. G01N 27/26
(52) U.S. Cl. ............................................. 204/451; 204/450
(58) Field of Search ..................................... 204/450, 468, 204/451

(56) References Cited

FOREIGN PATENT DOCUMENTS

| 442315A1 | 8/1991 | (EP) . |
| 518475A1 | 12/1992 | (EP) . |
| 9622524A1 | 7/1996 | (WO) . |

OTHER PUBLICATIONS

Simunicová et al. ("Separation of alkali and alkaline earth metal and ammonium cations by capillary zone electrophoresis with indirect UV absorbance detection", Journal of Chromatography A, 665 (1994) 203–209), Month unkown.*

Lin et al. ("Capillary electrophoretic analysis of inorganic cations: Role of complexing agent and buffer pH", journal of Chromatography A, 654 (1993) 167–176, Month unkown.*

P. Jandik et al., Capillary Electrophoresis of Small Molecules and Ions, VCH Publishers, New York, 1993, p. 287.

F. Foret et al., Capillary Zone Electrophoresis of Rare Earth Metals with Indirect UV Absorbance Detection, Electrophoresis 11 (1990), pp. 780–783.

L. Gross et al., Indirect Flurometric Detection of Cations in Capillary Zone Electrophoresis, Anal. Chem., 62 (1990), pp. 427–431.

A. Weston et al., Factors Affecting the Separtion of Inorganic Metal Cations by Capillary Electrophoresis, J. Chromatgraphy 593 (1992) pp. 289–295.

W. Beck et al., Capillary Electrophoresis of Organic and Inorganic Cations With Indirect UV Detection, Chromatography, 33(718) (1992) pp. 314–316.

Y. Shi et al., Separation of Metal Ions by Capillary Electrophoresis With a Complexing electrolyte, J. Chromatography, 640 (1993) pp. 473–479.

T. I. Lin, et al., Capillary electrophoretic Analysis of Inorganic Cations Role of Complexing Agent and Buffer pH, J. Chromatography A, 654 (1993), pp. 167–176.

Y. H. Lee et al., Determintation of Metal Cations by Capillary Electrophoresis Effect of Background Carrier and Complexing Agents, J. Chromatography A, 675 (1994) pp. 227–236.

C. Francois et al., Effect of the Concentration of 18–crown–6 Added to the Electrolyte Upon the Separation of Ammonium, Alkali and Alkaline–Earth Cations by Capillary Electrophoresis, J. Chromatography A, 706 (1995) pp. 535–553.

C. Francois et al., Separation of Transition Metal Cation by Capillary Electrophoresis Optimization of Complexing Agent Concentrations (Lactic Acid and 18–Crown–6), J. Chromatography A, 717 (1995) pp. 393–408.

Y. Shi, New Electrolyte Systems for the Determination of Metal Cations by Capillary Zone Electrophoresis, J. Chromatography A, 671 (1994) pp. 429–435.

T. Wang et al., Separation of Inorganic Phosphorus–Containing Anions by Capillary Electrophoresis, J. Chromatopraphy A, 834 (1999) pp. 233–241.

\* cited by examiner

*Primary Examiner*—Jill Warden
*Assistant Examiner*—Alex Noguerola
(74) *Attorney, Agent, or Firm*—Birch, Stewart, Kolasch & Birch, LLP

(57) ABSTRACT

Disclosed herein is electrophoresis buffer and a buffer kit useful in the analysis of small cations in samples containing simple or complex mixture of ions and/or neutral organic compounds in a short time and to scan unknown samples for the small cations by capillary electrophoresis with indirect optical detection. An embodiment of the disclosed CE buffer comprises complexing agents and chromophore co-ions. One of the complexing agents is a multidentate one of donor atoms of oxygen and nitrogen, particularly nitrilotriacetic acid (NTA). Other complexing agents, if any, can be crown ethers, for example, 18-crown-6. The chromophore co-ions can be produced by introducing nitrogen-containing heterocyclic compounds, in particular pyridine, to the electrophoresis buffer. The desired pH of the buffer kit is between about 2 and 4. In a particularly preferred embodiment, the buffer kit comprises a UV chromophore co-ion of nitrogen-containing heterocyclic compound of pyridine in a range of about 1 mM to about 40 mM, a multidentate complexing agent of donor atoms of oxygen and nitrogen of nitrilotriacetic acid (NTA) in a range of about 0.1 mM to about 5 mM and a crown ether of 18-crown-6 in a range of about 0.1 mM to about 50 mM. The desired pH is about 3. Indirect UV detection is made at 254 nm.

23 Claims, 3 Drawing Sheets

BUFFER FOR ANALYZING SMALL INORGANIC CATIONS BY CAPILLARY ELECTROPHORESIS

This application is the national phase under 35 U.S.C. § 371 of PCT International Application No. PCT/SG97/00067 which has an International filing date of Dec. 9, 1997, which designated the United States of America.

FIELD OF THE INVENTION

This invention relates to analysis of cations, in general, analysis of cations by capillary electrophoresis, and specifically to buffer useful in analyzing small inorganic cations of ammonium, alkali and alkaline-earth metal ions by capillary electrophoresis with indirect optical detection.

BACKGROUND OF THE INVENTION

Analysis of small inorganic cations of ammonium, alkali and alkaline-earth metal ions is commonly required for various purposes, such as control of food quality, clinical diagnosis and environmental monitoring. Analysis of small molecules and ions by capillary electrophoresis (CE) is of growing interest because of its simplicity, selectivity and low operation cost (P. Jandik and G. K. Bonn, Capillary Electrophoresis of Small Molecules and Ions, VCH Publishers, New York, 1993).

Studies on analysis of the small inorganic cations by CE focus primarily on finding solutions to low selectivity resulting from insufficient differences in mobilities of the hydrated cations and poor detectability due to lack of chromophores (F. Foret, S. Fanali, A. Nardi and P. Bocek, Capillary Zone Electrophoresis of Rare Earth Metals with Indirect UV Absorbance Detection, Electrophoresis, 11(1990) 780–783; L. Gross and E. S. Yeung, Indirect Fluorometric Detection of Cations in Capillary Zone Electrophoresis, Anal. Chem., 62 (1990) 427–431; A. Weston, P. R. Brown, P. Jandik, W. R. Jones and A. L. Heckenberg, Factors Affecting the Separation of Inorganic Metal Cations by Capillary Electrophoresis, J. Chromotogr. 593 (1992) 289–295).

As complexes have usually different charge to mass ratio from those of the hydrated cations, effective mobilities of the cations can be manipulated to enhance selectivity in CE separation of the small inorganic cations by introducing proper complexing agents in CE buffer. The complexing agents mainly includes multidentate complexing agents of donor atoms of oxygen. To differentiate ammonium from potassium ions, addition of a crown ether to buffer is effective.

A common and simple solution to poor detectability of the small cations is to provide chromophore co-ions of strong UV/visible absorption (or fluorescence) in electrophoresis buffer and to make use of indirect optical detection. The no-absorbing cations displace the chromophore co-ions while the cations are driven to move in electrophoresis buffer by electrophoretic force and electroosmotic flow (EOF). The cations are detected by decrease of absorbance. Chromophore co-ions for separation and detection of the small cations are usually nitrogen-containing heterocyclic compounds and substitutes of benzylamines.

Other variables are also known to affect selectivity and detectability in the separation of the small inorganic cations by CE. Variables related to buffer are pH, pH buffering capacity, ionic strength and conductivity, mobilities and $pK_a$'s of co-ions, wavelengths of absorption maxima and molar absorption coefficients of co-ions, concentrations of complexing agents and co-ions, etc. Variables related to capillary electrophoresis system are temperature, voltage, capillary dimensions, etc. Some variables are independent ones. Some are not. Development of buffer used for the analysis of the small inorganic cations with high selectivity and detectability needs the overall optimization of the variables above.

The analysis of the small inorganic cations of ammonium ions, alkali and alkaline-earth metal ions by CE with indirect optical detection has been an object of several research papers and patents. Beck and Engelhardt proposed the imidazolium cation as a chromophore co-ion of electrophoresis buffer for the separation of alkali and alkaline-earth metal cations (W. Beck and H. Engelhard, Capillary electrophoresis of organic and inorganic cations with indirect UV detection, Chromatographia, 33(7/8) (1992) 314–316). Jones et al. documented 4-methylbenzylamine as a chromophore co-ion and a group of complexing agents (citrate, succinate, tartrate, hydroxyisobutyrate, and oxalate) for the separation of cations in their patents (W. R. Jones, P. Jandik, M. Merion and A. Weston, Method for separating ionic species using capillary electrophoresis, European Patent 0442315 A1; W. R. Jones and P. Jandik, Method for separating ionic species using capillary electrophoresis, U.S. Pat. No. 5,156,724). Shi and Fritz compared different chromophores (phenylethylamine, benzyl amine, p-toluidine and 4-methylbenzyl amine) and complexing agents (hydroxyisobutyric, phthalic, malonic, tartaric, lactic and succinic acids) for the separation of alkali, alkaline-earth and other metal ions (Y. Shi and J. S. Fritz, Separation of metal ions by capillary elecrtrophoresis with a complexing electrolyte, J. Chromatogr., 640 (1993) 473–479). Lin et al. studied the role of complexing agents (acetic, glycolic, lactic, hydroxyisobutyric, oxalic, malonic, tartaric, and succinic acids) added to imidazole-based electrophoresis buffer in the separation of alkali and alkaline-earth metal cations (T. I. Lin et al, Y. H. Lee and Y. C. Chen, Capillary electrophoretic analysis of inorganic cations-Role of complexing agent and buffer pH, J. Chromatogr. A, 654 (1993) 167–176). In another study, Lee and Lin studied effects of chromophore co-ions (imidazole, benzylamine, ephedrine and pyridine) and complexing agents (glycolic, hydroxyisobutyric and succinic acids) (Y. H. Lee and T. I. Lin, Determination of metal cations by capillary electrophoresis -Effect of background carrier and complexing agents, J. Chromatogr. A. 675 (1994) 227–236). Francois et al. made a close study on effect of the concentrations of lactic acid and 18-crown-6 in electrophoresis buffer upon the separation of ammonium, alkali and alkali-earth cations by CE (C. Francois, Ph. Morin and M. Dreux, Effect of the concentration of 18-crown-6 added to the electrolyte upon the separation of ammonium, alkali and alkaline-earth cations by capillary electrophoresis, J. Chromatogr. A. 706 (1995) 535–553; C. Francois, Ph. Morin and M. Dreux, Separation of transition metal cations by capillary electrophoresis-Optimization of complexing agent concentrations (lactic acid and 18-crown-6) J. Chromatogr. A. 717 (1995) 393–408). Shi and Fritz, and Yang et al. studied on effect of aqueous-organic media on the separation of ammonium and metal ions (Y. Shi and J. S. Fritz, New electrolyte systems for the determination of metal cations by capillary zone electrophoresis, J. Chromatogr. A. 671 (1994) 429–435; Q. Yang, J. Smeyers-Verbeke, W. Wu, M. S. Khots and D. L. Massart, Simultaneous separation of ammonium and alkali, alkaline earth and transition metal ions in aqueous-organic media by capillary ion analysis, J. Chromatogr. A. 688 (1994) 339–349). All the above mentioned electrophoresis buffer systems contained multidentate complexing agents of donor atoms of only oxygen. Wang and Li studied migration behavior of alkali and alkaline-earth metal ion-EDTA complexes (T. Wang and S.F.Y. Li, Migration behavior of alkali and alkaline-earth metal ion-EDTA complexes and quantitative analysis of magnesium in real samples by capillary electrophoresis with indirect ultraviolet detection, J. Chromatogr. A. 707 (1995) 343–353). EDTA is a widely used multidentate complexing agent of donor atoms of oxygen and nitrogen. The results showed that EDTA-pyridine buffer system was not suitable to separate and determine calcium due to very high stability of EDTA-Ca complex. None of the published CE methods using available buffer systems has demonstrated the capability of separating all eight of the common small inorganic cations ($NH_4^+$, $Li^+$, $Na^+$, $K^+$, $Mg^{2+}$, $Ca^{2+}$, $Sr^{2+}$ and $Ba^{2+}$) with satisfactory resolution for the purposes of qualitatively screening or quantitatively determining the cations in real samples, especially for samples of complex matrices and high variation of concentrations of the cations. Therefore, there is a need for invention of CE buffer to be used for analyzing the small inorganic cations in real samples with higher selectivity and resolution than the available buffer systems.

OBJECT OF THE INVENTION

It is a primary object of the invention to provide optimized electrophoresis buffer at low cost for the use in analyzing small inorganic cations by capillary electrophoresis with indirect optical detection. The selectivity and detectability of a CE method using the buffer of the present invention are high enough to meet needs of analyzing the small inorganic cations in real samples of common analytical laboratory practice.

SUMMARY OF THE INVENTION

Capillary electrophoresis buffer satisfying the above need for analyzing small inorganic cations are disclosed. The buffer is characterized by using at least a multidentate complexing agent of donor atoms of oxygen and nitrogen for enhancing selectivity and a chromophore co-ion facilitating indirect optical detection, particularly indirect UV/visible spectroscopy.

An embodiment of the disclosed CE buffer comprises complexing agents and chromophore co-ions. One of the complexing agents is a multidentate one of donor atoms of oxygen and nitrogen, particularly nitrilotriacetic acid. Other complexing agents, if any, can be crown ethers, for example, 18-crown-6. The chromophore co-ions can be produced by introducing nitrogen-containing heterocyclic compounds, in particular pyridine, to the electrophoresis buffer.

In a particularly preferred embodiment, the buffer comprises 0.1–5 mM of nitrilotriacetic acid, 0.1–50 mM of 18-crown-6, and 1–40 mM of pyridine in a proper combination. The desired pH of the buffer is between about 2 and about 4. Detection in CE is made, in the particular case, at 254 nm. The temperature range for a CE method using the disclosed buffer is preferably conducted at between about 4° C. to 60° C., and most conveniently at about ambient (room) temperature.

The disclosed CE buffer compositions can be constructed into a kit. The kit contains mainly nitrilotriacetic acid and 1 8-crown-6, and pyridine. Such a kit is useful in the CE analysis of small inorganic cations, even in high variation of concentrations, in samples containing simple or complex mixture of ions and neutral organic compounds in a short time.

Advantages of the CE buffer and method are improved selectivity, high resolution, enhanced detectability, wide linearity of response function and good robustness in the separation of small inorganic cations in real samples.

DETAILED DESCRIPTION OF THE INVENTION

Figure 1:
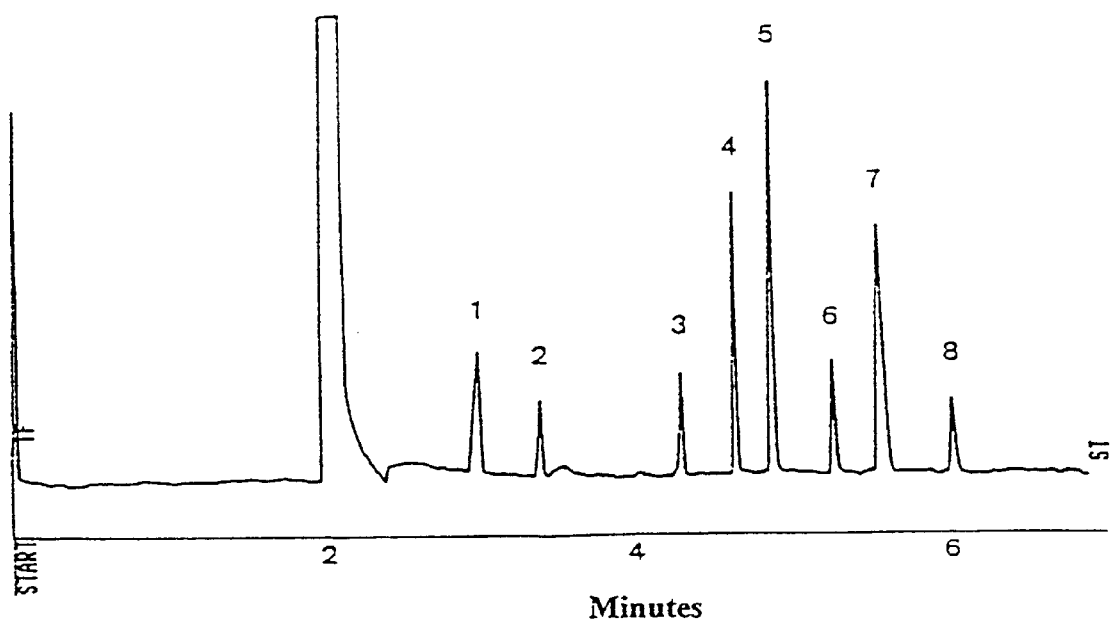
FIG. 1 is am electropherogram showing the separation and detection of a standard mixture of eight small inorganic cations: 1. ammonium ($NH_4^+$); 2. potassium ($K^+$, 10 ppm); 3. sodium ($Na^+$, 5 ppm); 4. calcium ($Ca^{2+}$, 10 ppm); 5. magnesium ($Mg^{2+}$, 10 ppm); 6. strontium ($Sr^{2+}$, 10 ppm); 7. lithium ($Li^+$, 5 ppm); 8. barium ($Ba^{2+}$, 10 ppm) by CE using the disclosed buffer comprising 10 mM pyridine, 3mM nitrilotriacetic acid (NTA) and 3 mM 18-crown-6.

The buffer of the present invention can be empolyed in a capillary electrophoresis (CE) method using indirect optical detection to simultaneously separate and detect small inorganic cations of similar properties contained in a sample. An early study on separation and detection of cations by CE with indirect UV detection was made by Foret et al. (F. Foret et al, 1990). Beck and Engelhardt reported imidazole-based buffer used in capillary electrophoresis of organic and inorganic cations with indirect UV detection(W. Beck and H. Engelhard, 1992). Jones et al. documented a CE method in which 4-methylbenzylamine was claimed to be a chromophore co-ion and a compound was selected out of a group of multidentate chelating agents of donor atoms of oxygen to be a component of the carrier electrolyte (W. R. Jones et al).

A CE method using the buffer of the present invention can be generally carried out in the following way: Fill a capillary of about 5 to about 200 μm ID with electrophoresis buffer; Then inject sample solution of the small cations of ammonium, alkali or/and alkaline-earth metal ions at the injection end of the capillary in either the hydrodynamic or the electrokinetic mode. In hydrodynamic mode an injection of the sample solution is made by raising sample solution and the injection end of the capillary to a height relative to the detection end of the capillary for a while or an injection is made by applying pressure to the sample solution to bring the sample solution into the injection end of the capillary or by applying a negative pressure of vacuum at the detection end of the capillary to suck the sample solution into the injection end of the capillary. In electrokinetic mode an injection is made by applying a voltage to the ends of the capillary to bring the cations into the capillary by electrophoretic movement and electroosmotic flow (EOF), a bulk flow of the buffer inside the capillary induced by electric field. Connect the injection end and the other end of the capillary to the buffer in the anodic and cathodic buffer compartment where the anode and the cathod of a power supply reside, respectively. Apply an voltage of 1 kV to 50 kV to the ends of the capillary to obtain a high electric field strength along the capillary and conduct current in the electrophoresis buffer inside the capillary to bring the cations of interest to travel from the injection end toward the detection end. On-line monitor optical signal at appropriate wavelength at a place near to the detection end of the capillary. Record the optical signal with a chart recorder or integrator or collect the optical signal with a microcomputer.

The disclosed buffer contains complexing agents enhancing selectivity and chromophore co-ions making indirect optical detection, in particular indirect UV detection, possible in the CE separation and determination of small inorganic cations. Complexes have usually different charge to mass ratio from those of the hydrated cations. Hence, effective mobilities of the cations can be manipulated to enhance selectivity in CE separation of the cations by introducing proper complexing agents in CE buffer. Unlike the multidentate complexing agents of donor atoms of oxygen reported by other research groups, the disclosed buffer contains essentially a multidentate complexing agent of donor atoms of oxygen and nitrogen, particularly nitrilotriacetic acid. Other complexing agents, if any, can be crown ethers, such as 18-crown-6. Concentrations in the combination of nitrilotriacetic acid and 1 8-crown-6 are also critical to the selectivity and consequently to the resolution in the CE separation of the cations. A chromophore co-ion making indirect UV detection of the small inorganic cations available can be a nitrogen-containing heterocyclic compound, particularly pyridine. Desired pH of the buffer can be adjusted by adding diluted inorganic acids (for example perchloric acid, hydrochloric acid or nitric acid) or organic acids (for example formic acid or acetic acid).

In a particular embodiment of the disclosed buffer, one complexing agent is nitrilotriacetic acid in a concentration range of 0.1 mM to 5 mM. Another complexing agent is 18-crown-6 in a concentration range of 0.1 mM to 50 mM. A chromophore co-ion is pyridine in a concentration range of 1 mM to 40 mM. Desired pH range is between about 2 to about 4. Detection is made, in the particular embodiment, at 254 nm. The temperature range for a CE method using the disclosed buffer is preferably conducted at between about 4° C. to 60° C., and most conveniently at about ambient (room) temperature.

A CE method using the disclosed CE buffer can be utilized to analyze the small inorganic cations in samples containing simple or complex mixture of ions and neutral organic compounds and to scan unknown samples for these cations in a short time. The small inorganic cations migrate in the disclosed buffer from the injection end toward the detection end of the capillary at fast speeds than those of transition metal ions and other large cations. Neutral compounds and anions migrate at even slower speeds. Advantages of the CE buffer and method are improved selectivity, high resolution, enhanced detectability, reduced analysis time, wide linearity of response function, minimized interference and good robustness in the separation of the small cations in real samples.

The practical usefulness of such increased selectivity and resolution obtained by a CE method using the present buffer can be illustrated, for example, using a tapwater sample and a seawater sample. Both the samples can be separated with sufficiently high resolution for the purpose of qualitatively screening and quantitatively determining the small inorganic cations.

EXAMPLES

The following examples are helpful in the illustration of the invention disclosed herein, but not construed as a limit to the disclosure, or the claims to follow:

Example 1
Separation and detection of a standard mixture of ammonium, alkali and alkaline-earth metal ions by CE using the disclosed buffer A standard mixture of the following eight small inorganic cations was prepared: ammonium ($NH_4^+$), lithium ($Li^+$), sodium ($Na^+$), potassium ($K^+$), magnesium ($Mg^{2+}$), calcium ($Ca^{2+}$), strontium ($Sr^{2+}$) and barium ($Ba^{2+}$).

All solutions were prepared using water of resistivity higher than 18 MΩ obtained with a NANOpure ultrapure water system (OMEGA). Electrophoresis was performed in a fused silica capillary of 50 μm ID (Polymicro Technologies). Effective length of the capillary was 45.0 cm and total length 57.0 cm. The detection window of 2 mm was made by stripping the external polyimide coating. The capillary was installed into the flow-cell of the LINEAR UVIS 200 Detector (Linear Instruments). The capillary was then sequentially purged for precondition with water (2 minutes), 0.1 M sodium hydroxide (5 minutes), water (2 minutes), and followed with the buffer (5 minutes). The buffer comprised 10 mM pyridine and 3 mM nitrilotriacetic acid (NTA) and 3 mM 18-crown-6 (pH=3). Between runs the capillary was washed with only the buffer. The sample solution was introduced into the injection end of the capillary in hydrodynamic mode by raising the injection end immersed in the sample solution to a height of 4.0 cm relative to the other end of the capillary for 20 seconds. The injection end of the capillary was then lowered to the same level as the other end. The injection end and the other end of the capillary were connected to the buffer in anodic and cathodic buffer compartments where the anode and the cathod of the power supply reside, respectively. A voltage of 18 kV was immediately applied to the ends of the capillary to conduct current in the electrophoresis buffer inside the capillary and to bring the cations of interest to travel from the injection end toward the detection end of the capillary. The detection of the cations was made in indirect optical mode by on-capillary monitoring absorbance at 254 nm. The electropherogram was obtained with HP 3390 A Integrator (Hewlett Packard). The electropherogram obtained is shown in FIG. 1.

The separation was completed in about 6 minutes. The resolution between any peak pairs of interest was greater than 2. Peak identifications in FIG. 1 are as following: 1. ammonium ($NH_4^+$, 10 ppm); 2. potassium ($K^+$, 10 ppm); 3. sodium ($Na^+$, 5 ppm); 4. calcium ($Ca^{2+}$, 10 ppm); 5. magnesium ($Mg^{2+}$, 10 ppm); 6. strontium ($Sr^{2+}$, 10 ppm); 7. lithium ($Li^+$, 5 ppm); 8. barium ($Ba^{2+}$, 10 ppm).

Figure 2:
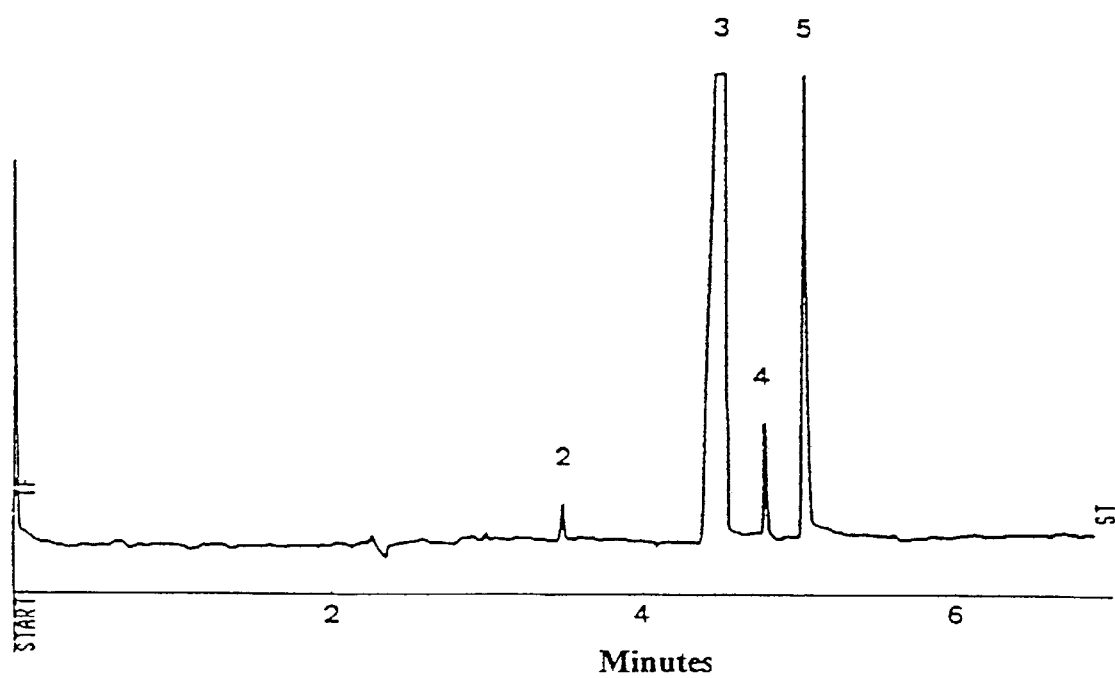
FIG. 2 is the electropherogram showing the peak identifications of: 2. potassium ($K^+$, 10 ppm); 3. sodium ($Na^+$, 5 ppm); 4. calcium ($Ca^{2+}$, 10 ppm); 5. magnesium ($Mg^{2+}$, 10 ppm) in a seawater sample by CE using the disclosed buffer.

Example 2
Separation and detection of sodium ($Na^+$), potassium ($K^+$), magnesium ($Mg^{2+}$), calcium ($Ca^{2+}$) in a seawater sample by CF using the disclosed buffer A seawater sample was filtrated with 0.45 μm nylon syringe filter (Cole-Parmer International), then diluted by 100 times with water. The other experimental conditions were the same as those in Example 1. The electropherogram obtained is shown in FIG. 2. Peak identifications: 2. potassium ($K^+$); 3. sodium ($Na^+$); 4. calcium ($Ca^{2+}$); 5. magnesium ($Mg^{2+}$).

Figure 3:
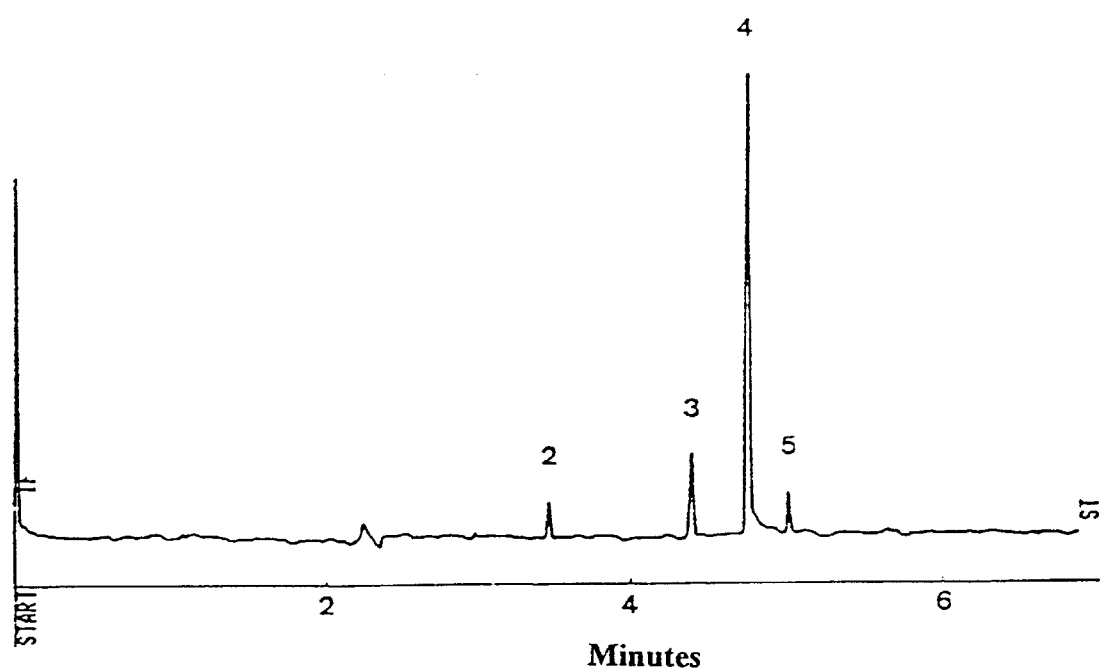
FIG. 3 is the electropherogram showing the peak identifications of: 2. potassium ($K^+$, 10 ppm); 3. sodium ($Na^+$, 5 ppm); 4. calcium ($Ca^{2+}$, 10 ppm); 5. magnesium ($Mg^{2+}$, 10 ppm) in a tapwater sample by CE using the disclosed buffer.

Example 3
Separation and detection of sodium ($Na^+$), potassium ($K^+$), magnesium ($Mg^{2+}$), calcium ($Ca^{2+}$) in a tapwater sample by CE using the disclosed buffer A seawater sample was filtrated with 0.45 μm nylon syringe filter (Cole-Parmer International). The other experimental conditions were the same as those in Example 1. The electropherogram obtained is shown in FIG. 3. Peak identifications: 2. potassium ($K^+$); 3. sodium ($Na^+$); 4. calcium ($Ca^{2+}$); 5. magnesium ($Mg^{2+}$).

What is claimed is:

1. An electrophoresis buffer comprising at least one complexing agent having donor atoms of oxygen and nitrogen and at least one nitrogen-containing UV chromophore co-ion.

2. The buffer of claim 1, wherein the UV chromophore co-ion is a nitrogen-containing heterocyclic compound.

3. The buffer of claim 1, wherein the complexing agent is a multidentate complexing agent having donor atoms of oxygen and nitrogen.

4. The buffer of claim 1, wherein a crown ether is added as an additional complexing agent.

5. A method of using the buffer of claim 1 comprising the steps of:
applying the buffer to an electrophoresis column; and
adding a sample to the column, wherein the sample contains a basic, acidic, or neutral solution.

6. A method for separating small cations in a sample comprising the steps of:
applying the buffer of claim 1 to a capillary electrophoresis column;
applying a sample solution containing small cations of ammonium, alkali, or alkaline earth metal ions at the injection end of the capillary; and
applying voltage across the capillary thereby electrophoretically separating the small cations.

7. The method of claim 6, wherein the sample contains ammonium ions, or common alkali metal ions selected from the group consisting of $Li^+$, $Na^+$, $K^+$, or alkaline-earth metal ions selected from the group consisting of $Mg^{2+}$, $Ca^{2+}$, $Sr^{2+}$, and $Ba^{2+}$.

8. The method of claim 7, wherein the capillary is fused silica and the internal diameter of the capillary is about 5 $\mu$m to about 200 $\mu$m.

9. The method of claim 8, wherein the voltage is between 1–50 kV.

10. A kit for use in capillary electrophoresis comprising reagents for preparing an electrophoresis buffer of pH 2–4, said reagents comprising at least one complexing agent and at least one UV chromophore co-ion, and optionally a crown ether wherein the complexing agent is a multidentate complexing agent having donor atoms of oxygen and nitrogen and the UV chromophore co-ion is a nitrogen-containing heterocyclic compound.

11. The kit of claim 10, wherein the nitrogen-containing heterocyclic compound is pyridine in a concentration of 1 mM to 40 mM in the prepared buffer.

12. The kit of claim 10, wherein the multidentate complexing agent is nitrolotriacetic acid (NTA).

13. The kit of claim 12, wherein the nitrolotriacetic acid is present at a concentration from 0.1 mM to 5 mM in the prepared buffer.

14. The kit of claim 12, wherein the crown ether is present and is 18crown-6 at a concentration of 0.1 mM to about 50 mM in the prepared buffer.

15. The kit of claim 12, wherein the pH of the prepared buffer is about 3.

16. An electrophoresis buffer comprising nitrolotriacetic acid and at least one UV chromophore co-ion.

17. The buffer of claim 16, wherein the UV chromophore co-ion is a nitrogen-containing heterocyclic compound.

18. The buffer of claim 16, wherein a crown ether is added as an additional complexing agent.

19. The buffer of claim 16, having a pH of from 2 to 4.

20. A method of using the buffer of claim 16, comprising the steps of:
applying the buffer of claim 16 to an electrophoresis column; and
adding a sample to the column, wherein the sample contains an inorganic acid, an organic acid, a mixture or organic acids, a mixture of inorganic acids, or a mixture of organic and inorganic acids.

21. A method for separating small cations in samples using capillary electrophoresis and indirect optical detection comprising the steps of:
applying the buffer of claim 16 to a capillary electrophoresis column;
applying a sample solution containing small cations of ammonium, alkali, or alkaline earth metal ions at the injection end of the capillary; and
applying voltage across the capillary thereby electrophoretically separating the small cations.

22. A kit for use in capillary electrophoresis comprising reagents for preparing an electrophoresis buffer comprising nitrolotriacetic acid and at least one UV chromophore co-ion, and optionally containing a crown ether.

23. The kit of claim 22, wherein the pH of the buffer is from 2 to 4.

* * * * *